(12) United States Patent
Auerbach et al.

(10) Patent No.: US 12,285,258 B2
(45) Date of Patent: Apr. 29, 2025

(54) 3D INTRACARDIAC ACTIVITY PRESENTATION

(71) Applicant: BIOSENSE WEBSTER (ISRAEL) LTD., Yokneam (IL)

(72) Inventors: Shmuel Auerbach, Kerem Maharal (IL); Stanislav Goldberg, Haifa (IL); Oded Baron, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 316 days.

(21) Appl. No.: 16/580,151

(22) Filed: Sep. 24, 2019

(65) Prior Publication Data
US 2021/0085204 A1     Mar. 25, 2021

(51) Int. Cl.
*A61B 5/287*     (2021.01)
*A61B 5/00*      (2006.01)
(Continued)

(52) U.S. Cl.
CPC ............ *A61B 5/287* (2021.01); *A61B 5/0033* (2013.01); *A61B 5/061* (2013.01); *A61B 5/318* (2021.01);
(Continued)

(58) Field of Classification Search
CPC ....... A61B 5/287; A61B 5/0033; A61B 5/318; A61B 5/339; A61B 5/061; A61B 5/6859;
(Continued)

(56) References Cited

U.S. PATENT DOCUMENTS 5,357,428 A * 10/1994 Stone, Jr. ............... A61B 5/291
                                                     600/372
5,782,773 A    7/1998 Kuo
(Continued)

FOREIGN PATENT DOCUMENTS

CN      105378793 B     5/2019
EP        3254618 A1   12/2017
(Continued)

OTHER PUBLICATIONS

European Search Report for corresponding EPA No. 20197871.5 dated Feb. 22, 2021.

*Primary Examiner* — Serkan Akar
*Assistant Examiner* — Aminah Asghar
(74) *Attorney, Agent, or Firm* — Dergosits & Noah LLP; Todd A. Noah

(57) ABSTRACT

In one embodiment, a medical system includes a catheter configured to be inserted into a chamber of a heart of a living subject, and including catheter electrodes configured to contact tissue at respective locations within the chamber of the heart, a display, and processing circuitry configured to receive signals from the catheter, and in response to the signals, sample voltage values of the signals at respective sampling times, compute respective curved three-dimensional surfaces describing electrical activity of the tissue over the catheter electrodes at respective ones of the sampling times, responsively to (a) respective positions of the respective catheter electrodes, and (b) the respective sampled voltage values indicative of electrical activity of the tissue that is sensed by the respective catheter electrodes at the respective locations at the respective sampling times, and render the respective three-dimensional surfaces to the display over time.

19 Claims, 7 Drawing Sheets

(51) Int. Cl.
  *A61B 5/06* (2006.01)
  *A61B 5/318* (2021.01)
  *A61B 5/339* (2021.01)
  *A61B 18/00* (2006.01)
  *A61B 18/14* (2006.01)

(52) U.S. Cl.
  CPC ............ *A61B 5/339* (2021.01); *A61B 5/6859* (2013.01); *A61B 18/1492* (2013.01); *A61B 5/6853* (2013.01); *A61B 5/6858* (2013.01); *A61B 5/743* (2013.01); *A61B 2018/00267* (2013.01); *A61B 2018/00357* (2013.01); *A61B 2018/00839* (2013.01); *A61B 2018/00875* (2013.01)

(58) Field of Classification Search
  CPC . A61B 18/1492; A61B 5/6853; A61B 5/6858; A61B 5/743; A61B 2018/00267; A61B 2018/00357; A61B 2018/00839; A61B 2018/00875; A61B 5/6869; A61B 5/349; A61B 2018/00577; A61B 2018/00351
  See application file for complete search history.

(56) References Cited

U.S. PATENT DOCUMENTS

| | | |
|---|---|---|
| 6,226,542 B1 | 5/2001 | Reisfeld |
| 6,301,496 B1 | 10/2001 | Reisfeld |
| 6,814,733 B2 | 11/2004 | Schwartz |
| 6,892,091 B1 | 5/2005 | Ben-Haim et al. |
| 6,997,924 B2 | 2/2006 | Schwartz |
| 7,156,816 B2 | 1/2007 | Schwartz |
| 7,536,218 B2 | 5/2009 | Govari |
| 7,756,576 B2 | 7/2010 | Levin |
| 2009/0262979 A1* | 10/2009 | Markowitz ............ A61B 5/061 382/128 |
| 2011/0021936 A1 | 1/2011 | Luo |
| 2011/0106203 A1* | 5/2011 | Markowitz ............... A61B 5/06 607/27 |
| 2012/0130232 A1 | 5/2012 | Markowitz |
| 2013/0041235 A1* | 2/2013 | Rogers ................ A61B 5/1107 600/306 |
| 2015/0254893 A1 | 9/2015 | Laughner |
| 2015/0313491 A1 | 11/2015 | Edwards |
| 2016/0183824 A1* | 6/2016 | Severino ............. A61B 5/7246 600/523 |
| 2017/0079542 A1 | 3/2017 | Spector |
| 2017/0128128 A1* | 5/2017 | Saba ...................... A61B 34/20 |
| 2019/0290154 A1* | 9/2019 | Wang .................... A61B 5/316 |
| 2021/0118572 A1* | 4/2021 | Afonso ................. A61B 5/339 |
| 2021/0236053 A1* | 8/2021 | Narayan ............... A61B 5/363 |

FOREIGN PATENT DOCUMENTS

| | | |
|---|---|---|
| EP | 3375365 A2 | 9/2018 |
| RU | 2541126 C2 | 2/2015 |
| WO | WO2017192769 A1 | 11/2017 |

* cited by examiner

3D INTRACARDIAC ACTIVITY PRESENTATION

FIELD OF THE INVENTION

The present invention relates to medical systems, and in particular, but not exclusively, to analysis of electrical activity.

BACKGROUND

Electrical activity at a point in the heart may be measured by advancing a multiple-electrode catheter to measure electrical activity at multiple points in the heart chamber simultaneously. Other methods, such as using an external vest may provide an indication of cardiac activity. A record derived from time varying electrical potentials as measured by one or more electrodes is known as an electrogram. Electrograms may be measured by unipolar or bipolar leads, and are used, e.g., to determine onset of electrical propagation at a point, known as local activation time (LAT).

U.S. Pat. No. 5,782,773 to Kuo, et al., describes a three-dimensional electrocardiogram display method for 3-D representation of a plurality of cardiac signals. In this method, a 3-D rectangular coordinate system is defined to display the 3-D representation of the cardiac signals. Further, an amplitude display scheme, preferably an amplitude-to-color mapping table, is defined to assign various quantization levels of amplitude to specified distinctive colors. By graphic processing and display means, the 3-D representation of the cardiac signals can be generated and displayed. The physicians can choose to observe the 3-D graph in various views, including perspective view, sectional view, and top rectangular view. This allows the physicians to make diagnosis of heart diseases by observing just one or two 3-D representations of the cardiac signals. The physicians can thus have an overall integral view over a plentiful number of cardiac signals and thereby make diagnosis about the heart conditions of the patient more easily.

US Patent Publication 2011/0021936 of Luo describes a device and method for displaying medical data for a stress test monitoring system. A computer-implemented method and apparatus for displaying electrical impulse data of a human heart for analysis includes receiving cardiac electrical impulse data produced during a cardiac stress test by a plurality of electrode leads adapted for placement on a patient and calculating parameters for a plurality of display windows based on the data and providing a main display in which the plurality of display windows are positioned. A three-dimensional color mapping plot is displayed in one of the plurality of display windows and a two dimensional color mapping plot is displayed in another of the plurality of display windows. Additionally, a plot of raw lead data from at least one lead is displayed in one of the plurality of display windows.

US Patent Publication 2012/0130232 of Markowitz, et al., describes a volume of a patient that can be mapped with a system operable to identify a plurality of locations and save a plurality of locations of a mapping instrument. The mapping instrument can include one or more electrodes that can sense a voltage that can be correlated to a three-dimensional location of the electrode at the time of the sensing or measurement. Therefore, a map of a volume can be determined based upon the sensing of the plurality of points without the use of other imaging devices. An implantable medical device can then be navigated relative to the mapping data.

International Patent Publication WO 2017/192769 of Acutus Medical Inc., describes a localization system and method useful in the acquisition and analysis of cardiac information. The localization system and method can be used with systems that perform cardiac mapping, diagnosis and treatment of cardiac abnormalities, as examples, and in the retrieval, processing, and interpretation of such types of information. The localization system and method use high impedance inputs, improved isolation, and relatively high drive currents for pairs of electrodes used to establish a multi-axis coordinate system. The axes can be rotated and scaled to improve localization.

SUMMARY

There is provided in accordance with an embodiment of the present disclosure, a medical system, including a catheter configured to be inserted into a chamber of a heart of a living subject, and including catheter electrodes configured to contact tissue at respective locations within the chamber of the heart, a display, and processing circuitry configured to receive signals from the catheter, and in response to the signals sample voltage values of the signals at respective sampling times, compute respective curved three-dimensional surfaces describing electrical activity of the tissue over the catheter electrodes at respective ones of the sampling times, responsively to (a) respective positions of the respective catheter electrodes, and (b) the respective sampled voltage values indicative of electrical activity of the tissue that is sensed by the respective catheter electrodes at the respective locations at the respective sampling times, and render the respective three-dimensional surfaces to the display over time.

Further in accordance with an embodiment of the present disclosure the processing circuitry is configured to color respective regions of the respective three-dimensional surfaces responsively to respective ones of the sampled voltage values.

Still further in accordance with an embodiment of the present disclosure the respective positions of the respective catheter electrodes are respective projected positions projected onto a plane, the processing circuitry is configured to compute respective displacements, perpendicular to the plane, from respective ones of the projected positions of respective ones of the catheter electrodes responsively to respective ones of the sampled voltage values at respective ones of the sampling times, and the processing circuitry is configured to fit the respective curved three-dimensional surfaces describing the electrical activity of the tissue over the catheter electrodes at the respective ones of the sampling times, responsively to respective ones of the displacements, perpendicular to the plane, from respective ones of the projected positions.

Additionally, in accordance with an embodiment of the present disclosure the processing circuitry is configured to color respective regions of the respective three-dimensional surfaces responsively to respective ones of the displacements.

Moreover, in accordance with an embodiment of the present disclosure the processing circuitry is configured to sample the voltage values of the signals at the respective sampling times at a rate exceeding ten times per second, and render the respective three-dimensional surfaces to the display over time with a new one of the three-dimensional surfaces being displayed at least every tenth of a second so that the rendered three-dimensional surfaces provide an animation of an activation wave associated with the electrical activity of the tissue over the catheter electrodes.

Further in accordance with an embodiment of the present disclosure, the system includes an interface configured to receive user input to change a viewing angle of ones of the three-dimensional surfaces, wherein the processing circuitry is configured to render ones of the three-dimensional surfaces with a different viewing angle responsively to the received user input.

Still further in accordance with an embodiment of the present disclosure the catheter includes a shaft having a distal end, and a distal end assembly on which the catheter electrodes are disposed, and the respective positions of the respective catheter electrodes are respective positions derived from a static computer model of the catheter.

Additionally, in accordance with an embodiment of the present disclosure the respective positions of the respective catheter electrodes are respective projected positions projected onto a plane perpendicular to an axis of the shaft.

Moreover, in accordance with an embodiment of the present disclosure the catheter includes a shaft having a distal end, and a distal end assembly on which the catheter electrodes are disposed, and the processing circuitry is configured to compute the respective positions of the respective catheter electrodes.

Further in accordance with an embodiment of the present disclosure the respective positions of the respective catheter electrodes are respective projected positions projected onto a plane perpendicular to an axis of the shaft.

There is also provided in accordance with another embodiment of the present disclosure a medical method, including receiving signals from a catheter, which is configured to be inserted into a chamber of a heart of a living subject, and including catheter electrodes configured to contact tissue at respective locations within the chamber of the heart, in response to the signals, sampling voltage values of the signals at respective sampling times, computing respective curved three-dimensional surfaces describing electrical activity of the tissue over the catheter electrodes at respective ones of the sampling times, responsively to (a) respective positions of the respective catheter electrodes, and (b) the respective sampled voltage values indicative of electrical activity of the tissue that is sensed by the respective catheter electrodes at the respective locations at the respective sampling times, and rendering the respective three-dimensional surfaces to a display over time.

Still further in accordance with an embodiment of the present disclosure, the method includes coloring respective regions of the respective three-dimensional surfaces responsively to respective ones of the sampled voltage values.

Additionally, in accordance with an embodiment of the present disclosure the respective positions of the respective catheter electrodes are respective projected positions projected onto a plane, the method further including computing respective displacements, perpendicular to the plane, from respective ones of the projected positions of respective ones of the catheter electrodes responsively to respective ones of the sampled voltage values at respective ones of the sampling times, and fitting the respective curved three-dimensional surfaces describing the electrical activity of the tissue over the catheter electrodes at the respective ones of the sampling times, responsively to respective ones of the displacements, perpendicular to the plane, from respective ones of the projected positions.

Moreover, in accordance with an embodiment of the present disclosure, the method includes coloring respective regions of the respective three-dimensional surfaces responsively to respective ones of the displacements.

Further in accordance with an embodiment of the present disclosure, the method includes sampling the voltage values of the signals at the respective sampling times at a rate exceeding ten times per second, wherein the rendering includes rendering the respective three-dimensional surfaces to the display over time with a new one of the three-dimensional surfaces being displayed at least every tenth of a second so that the rendered three-dimensional surfaces provide an animation of an activation wave associated with the electrical activity of the tissue over the catheter electrodes.

Still further in accordance with an embodiment of the present disclosure, the method includes receiving user input to change a viewing angle of ones of the three-dimensional surfaces, and rendering ones of the three-dimensional surfaces with a different viewing angle responsively to the received user input.

Additionally, in accordance with an embodiment of the present disclosure the catheter includes a shaft having a distal end, and a distal end assembly on which the catheter electrodes are disposed, and the respective positions of the respective catheter electrodes are respective positions derived from a static computer model of the catheter.

Moreover, in accordance with an embodiment of the present disclosure the respective positions of the respective catheter electrodes are respective projected positions projected onto a plane perpendicular to an axis of the shaft.

Further in accordance with an embodiment of the present disclosure the catheter includes a shaft having a distal end, and a distal end assembly on which the catheter electrodes are disposed, and the method further includes computing the respective positions of the respective catheter electrodes.

Still further in accordance with an embodiment of the present disclosure the respective positions of the respective catheter electrodes are respective projected positions projected onto a plane perpendicular to an axis of the shaft.

There is also provided in accordance with still another embodiment of the present disclosure a software product, including a non-transient computer-readable medium in which program instructions are stored, which instructions, when read by a central processing unit (CPU), cause the CPU to receive signals from a catheter, which is configured to be inserted into a chamber of a heart of a living subject, and including catheter electrodes configured to contact tissue at respective locations within the chamber of the heart, in response to the signals, sample voltage values of the signals at respective sampling times, compute respective curved three-dimensional surfaces describing electrical activity of the tissue over the catheter electrodes at respective ones of the sampling times, responsively to (a) respective positions of the respective catheter electrodes, and (b) the respective sampled voltage values indicative of electrical activity of the tissue that is sensed by the respective catheter electrodes at the respective locations at the respective sampling times, and render the respective three-dimensional surfaces to a display over time.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
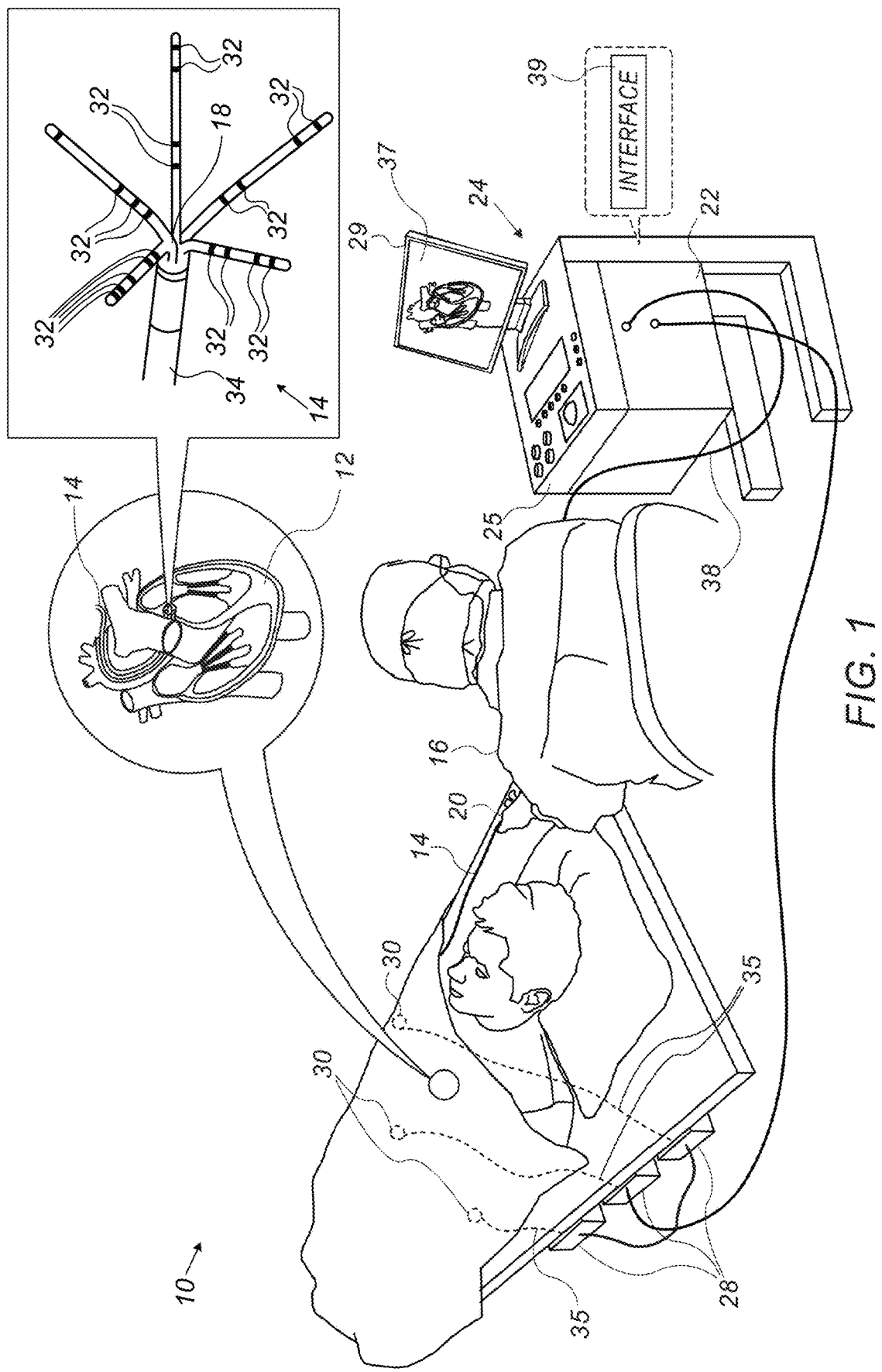
FIG. 1 is a partly pictorial, partly block diagram view of a cardiac analysis system constructed and operative in accordance with an embodiment of the present invention.

Presentation of electrical activity signals from complex multi spline catheters (e.g., a PENTARAY® catheter of Biosense Webster, Inc., Irvine, CA USA, or a basket catheter) or multi-electrodes on linear catheters in a way which is intuitive for the physician is challenging due to the geometric distribution of the electrodes. Presenting the electrical activity in a two-dimensional (2D) list, such as showing multiple intracardiac electrograms (IEGMs) does not reflect the geometry of the catheter.

Embodiments of the present invention solve the above problems by providing a three-dimensional (3D) presentation including respective curved three-dimensional surfaces which describe electrical activity of tissue over catheter electrodes at respective sampling times.

Intracardiac (IC) signals, which are received from the electrodes of a catheter are collected and sampled at different sampling times. The electrical activity of the catheter electrodes at one of the sampling times is plotted on the 3D presentation as a curved 3D surface. The 3D presentation may be defined by three axes (x, y and z) or any other suitable coordinate system. The x and y axes indicate the 2D position of the electrodes of the catheter (for example, by projecting the electrode position on to a plane defined by the x and y-axes). The z-axis indicates the voltage of the electrical activity captured by the electrodes at the sampled time. The curved 3D surface is computed by fitting the 3D surface to data points defined by the x-y coordinates of the electrode positions of the catheter electrodes and the respective z-coordinates of the sampled voltage. The fitting of the 3D surface may be performed by interpolating (and optionally extrapolating) between the data points mentioned above. Regions of the 3D surface may be optionally colored according to the voltage level associated with the regions.

The 3D presentation may be static (e.g. for single sampling times) or may be dynamic (e.g., a video) showing how the electrical activity moves as an activation wave over the electrodes of the catheter providing the physician with a useful diagnostic tool.

Any suitable catheter may be used in the above embodiments, for example, multi-spline catheters (e.g., a PENTARAY® catheter of Biosense Webster, Inc., Irvine, CA USA, or a basket catheter) or other multi-electrode catheters (e.g., balloon catheter, or Lasso catheter).

The catheter is inserted into the heart chamber of a living subject. The catheter may include a shaft having a distal end, and a distal end assembly on which catheter electrodes are disposed. The catheter electrodes contact tissue at respective locations within the heart chamber. Processing circuitry receives signals from the catheter, and in response to the signals, samples voltage values of the signals at respective sampling times.

In some embodiments, the processing circuitry computes respective positions of the respective catheter electrodes, for example, responsively to signal(s) received from a position transducer (such as a position sensor or sensors of the catheter or an externally placed sensor(s)).

In other embodiments, the positions of the respective catheter electrodes, used in the computations described below, are derived from a static computer model of the catheter. For example, if the catheter being used is a multi-spline catheter with deflectable splines, the positions used in the computations described below may be based on the positions of the deflectable splines in a non-deflected position even if the splines are in fact deflected at the respective sampling time.

Whether the positions are computed from the received signal(s) or derived from the static computer model, or any other suitable source, the positions of the catheter electrodes are typically projected positions projected onto a plane (e.g., the x-y axes described above). In some embodiments, the plane is perpendicular to an axis of the shaft of the catheter.

The processing circuitry computes respective curved three-dimensional surfaces describing electrical activity of the tissue over the catheter electrodes at respective ones of the sampling times. It should be noted that any one of the three-dimensional surfaces describes electrical activity for a corresponding one of the sampling times and not multiple sampling times. The sampled voltages of different sampling times yield different three-dimensional surfaces. The three-dimensional surfaces are computed responsively to: (a) respective positions (e.g., two-dimensional position coordinates) of the respective catheter electrodes; and (b) the respective sampled voltage values indicative of electrical activity of the tissue that is sensed by the respective catheter electrodes at the respective locations (on the tissue) at the respective sampling times. For example, one three-dimensional surface is computed responsively to: (a) respective positions (e.g., two-dimensional position coordinates) of the respective catheter electrodes; and (b) the respective sampled voltage values sampled at one of the respective sampling times.

In some embodiments, the processing circuitry colors respective regions of the respective three-dimensional surfaces responsively to respective ones of the sampled voltage values.

In some embodiments, the processing circuitry computes respective displacements, perpendicular to the plane (e.g., along the z axis away from the x-y axes), from respective projected positions of respective catheter electrodes responsively to respective sampled voltage values at respective sampling times. Each displacement provides a z-axis coordinate when a cartesian coordinate system is used. For example, a displacement $z_n$ is computed according to the sampled voltage, sampled at time t1, of the signal sensed by electrode number n of the catheter. Electrode number n has position coordinates $x_n, y_n$ on the plane defined by the x-y axes. Therefore, the data point of electrode number n in the 3D presentation for time t1 has coordinates $x_n, y_n, z_n$. The processing circuitry fits the respective curved three-dimensional surfaces describing the electrical activity of the tissue over the catheter electrodes at the respective sampling times, responsively to the respective computed displacements, perpendicular to the plane, from respective ones of the projected positions, e.g., according to the data points representing the electrical activity of each of the electrodes in the coordinate system. In some embodiments, the processing circuitry colors respective regions of the respective three-dimensional surfaces responsively to respective ones of the displacements.

The processing circuitry is configured to render the respective three-dimensional surfaces to the display over time. In some embodiments, the processing circuitry renders the respective three-dimensional surfaces to the display over time with a new one of the three-dimensional surfaces being displayed frequently enough (e.g., at least every one-tenth of a second) so that the rendered three-dimensional surfaces provide an animation of an activation wave associated with the electrical activity of the tissue over the catheter electrodes.

A user interface may receive user input to change a viewing angle of the three-dimensional surfaces, which may then be rendered with a different viewing angle responsively to the received user input.

System Description

Reference is now made to FIG. 1, which is a partly pictorial, partly block diagram view of a cardiac analysis system 10 constructed and operative in accordance with an embodiment of the present invention.

Turning now to the drawings, reference is initially made to FIG. 1, which is a pictorial illustration of a cardiac analysis system 10, constructed and operative in accordance with a disclosed embodiment of the invention, for computing and evaluating electrical activity and optionally for performing ablative procedures on a heart 12 of a living subject. The system comprises a catheter 14, such as a catheter, which is percutaneously inserted by an operator 16 through the patient's vascular system into a chamber or vascular structure of the heart 12. The operator 16, who is typically a physician, brings a distal tip 18 of the catheter 14 into contact with the heart wall, for example, at an ablation target site or to capture electrical potentials over time at multiple sample location over a surface of one or more chambers of the heart 12. Electrical activation maps may be prepared, according to the methods disclosed in U.S. Pat. Nos. 6,226,542, 6,301,496, and 6,892,091. One commercial product embodying elements of the system 10 is available as the CARTO® 3 System, available from Biosense Webster, Inc. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a temperature (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal tip 18 of the catheter 14 as desired for the ablation. To aid the operator 16, a distal portion of the catheter 14 contains position sensors (not shown) that provide signals to processing circuitry 22, located in a console 24. The processing circuitry 22 may fulfill several processing functions as described below.

Ablation energy and electrical signals can be conveyed to and from the heart 12 through catheter electrodes 32 located at or near the distal tip 18 via cable 34 to the console 24. In such a manner, the electrodes 32 are configured to contact tissue at respective locations with the chamber of the heart 12 and capture electrical potentials over time at the respective locations. Additionally, or alternatively, other electrodes may be configured to capture electrical potentials over time at multiple sample locations over a surface of one or more chambers of the heart 12. Pacing signals and other control signals may be conveyed from the console 24 through the cable 34 and the electrodes 32 to the heart 12. The catheter 14 may be implemented without ablation capabilities as an exploratory device having electrodes configured to capture electrical potentials over time at multiple sample locations over a surface of one or more chambers of the heart 12.

Wire connections 35 link the console 24 with body surface electrodes 30 and other components of a positioning sub-system for measuring location and orientation coordinates of the catheter 14. The processing circuitry 22 or another processor (not shown) may be an element of the positioning sub-system. The electrodes 32 and the body surface electrodes 30 may be used to measure tissue impedance at the ablation site as taught in U.S. Pat. No. 7,536,218. A sensor for bioelectric information, e.g., a temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in U.S. Pat. Nos. 6,814,733, 6,997,924, and 7,156,816.

In one embodiment, the positioning subsystem comprises a magnetic position tracking arrangement that determines the position and orientation of the catheter 14 by generating magnetic fields in a predefined working volume and sensing these fields at the catheter 14, using field generating coils 28. The positioning subsystem is described in U.S. Pat. Nos. 7,756,576 and 7,536,218.

As noted above, the catheter 14 is coupled to the console 24, which enables the operator 16 to observe and regulate the functions of the catheter 14. The processing circuitry 22 may be embodied as a computer with appropriate signal processing circuits. The processing circuitry 22 is coupled to drive a display 29 including a display screen 37. The signal processing circuits may receive, amplify, filter and digitize signals from the catheter 14, including signals generated by sensors such as electrical, temperature and contact force sensors, and location sensing electrodes (not shown) located distally in the catheter 14. The digitized signals are received and used by the console 24 and the positioning sub-system to compute the position and orientation of the catheter 14, and to analyze the electrical signals from the electrodes.

In order to generate electroanatomic maps, the processing circuitry 22 typically comprises an electroanatomic map generator, an image registration program, an image or data analysis program and a graphical user interface configured to present graphical information on the display 29.

In practice, some or all of these functions of the processing circuitry 22 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The console 24 may also include an interface 39 to receive input commands from the operator 16 via any suitable user input device, for example, but not limited to, a pointing device (such as a mouse of stylus), a keyboard, and/or a touch sensitive screen implemented in the display screen 37.

Typically, the system 10 includes other elements, which are not shown in the figures for the sake of simplicity. For example, the system 10 may include an electrocardiogram (ECG) monitor, coupled to receive signals from the body surface electrodes 30, in order to provide an ECG synchronization signal to the console 24. As mentioned above, the system 10 typically also includes a reference position sensor, either on an externally applied reference patch attached to the exterior of the subject's body, or on an internally placed catheter, which is inserted into the heart 12 and maintained in a fixed position relative to the heart 12. Conventional pumps and lines for circulating liquids through the catheter 14 for cooling the ablation site may be provided. The system 10 may receive image data from an external imaging modality, such as an MRI unit or the like and includes image processors that can be incorporated in, or invoked by, the processing circuitry 22 for generating and displaying images.

Figure 2B:
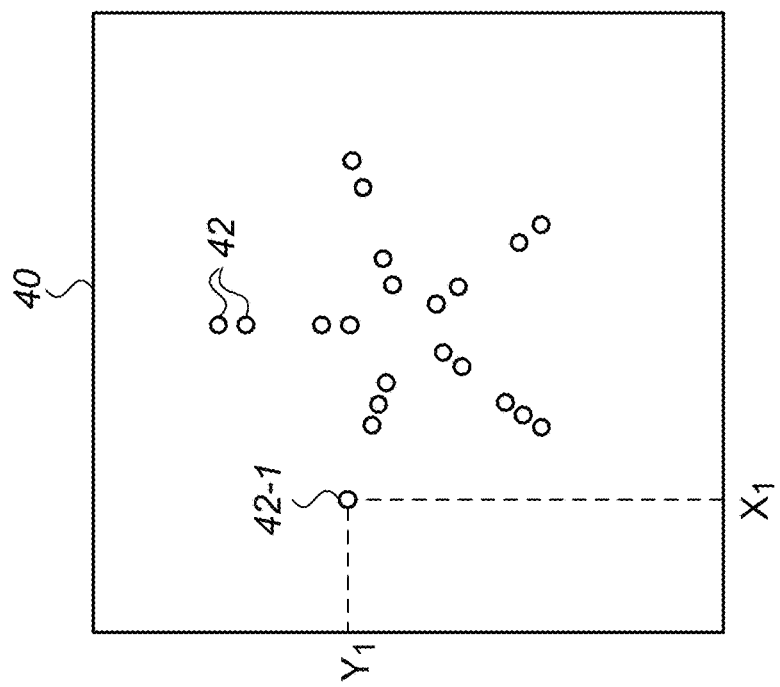
FIGS. 2A-B are schematic view illustrating projecting positions of electrodes to a plane for use in the system of FIG. 1.
Figure 2A:
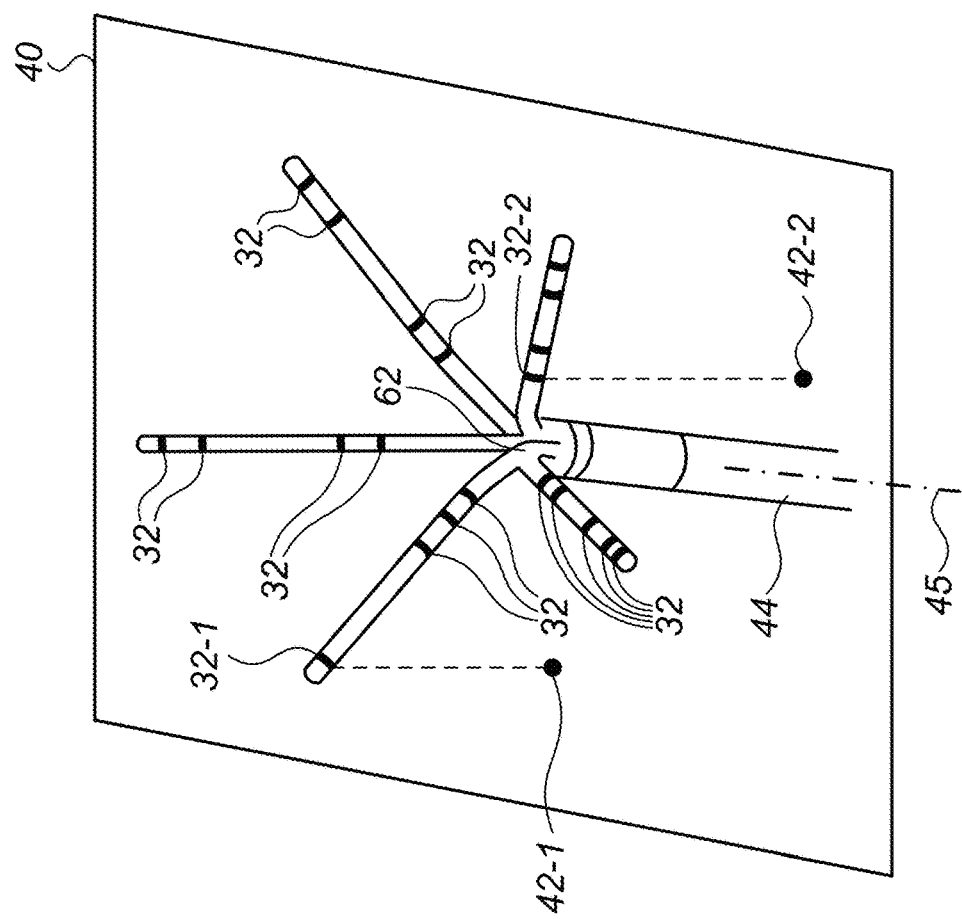

Reference is now made to FIGS. 2A-B, which are schematic view illustrating projecting positions of electrodes 32 to a plane 40 for use in the system 10 of FIG. 1. The catheter 14 shown in FIG. 2A includes a shaft 44 having a distal end 62, and a distal end assembly 64 which comprises multiple splines with the electrodes 32 disposed thereon. Any suitable distal end assembly may be used, for example, but not limited to, a basket distal end assembly, a balloon distal end assembly, or a lasso distal end assembly.

FIG. 2A shows projecting electrodes 32-1 and 32-2 onto positions 42-1, 42-2, respectively, on the plane 40, by projecting in a direction which is perpendicular to the plane 40 and parallel to an axis 45 of the shaft 44 of the catheter 14. The electrodes 32 may be projected at any suitable direction on to the plane 40. FIG. 2B shows the projected positions 42 (only some labeled for the sake of simplicity) of all the electrodes 32 of the catheter 14. The position 42-1 of the electrodes 32-1 has coordinates x1,y1 in the plane 40, which is defined as lying on the x and y-axes.

Figure 3:
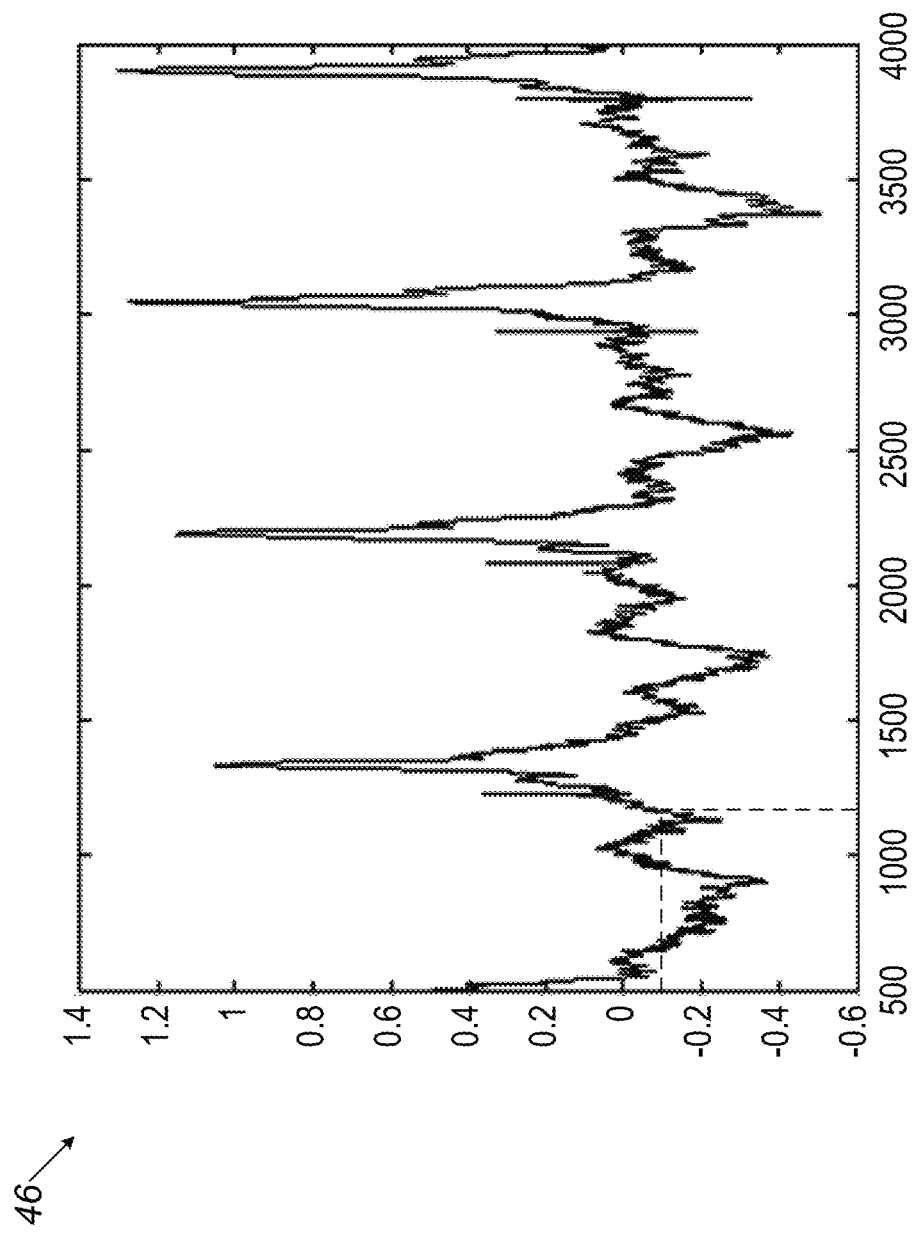
FIG. 3 is a schematic view of an intracardiac signal sampled in the system of FIG. 1.

Reference is now made to FIG. 3, which is a schematic view of an intracardiac (IC) signal 46 sampled in the system 20 of FIG. 1. Respective IC signals 46 are received from respective electrodes 32 (FIG. 1). FIG. 3 shows an example signal 46 received from the electrode 32-1 (FIG. 2A). FIG. 3 shows the signal 46 being sampled at 1200 milliseconds corresponding with a voltage of approximately −0.1 millivolts. Similarly, in this example, the signals received from the other electrodes 32 are also sampled at 1200 milliseconds to find the voltage for the other electrodes 32.

Figure 4B:
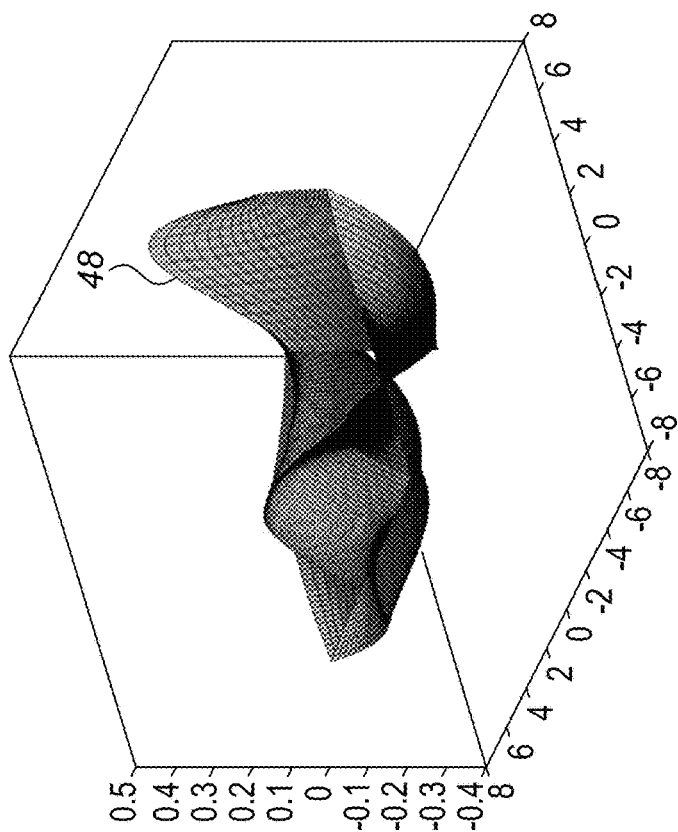
FIGS. 4A-F are schematic views of curved three-dimensional surfaces describing electrical activity rendered by the system of FIG. 1.
Figure 4A:
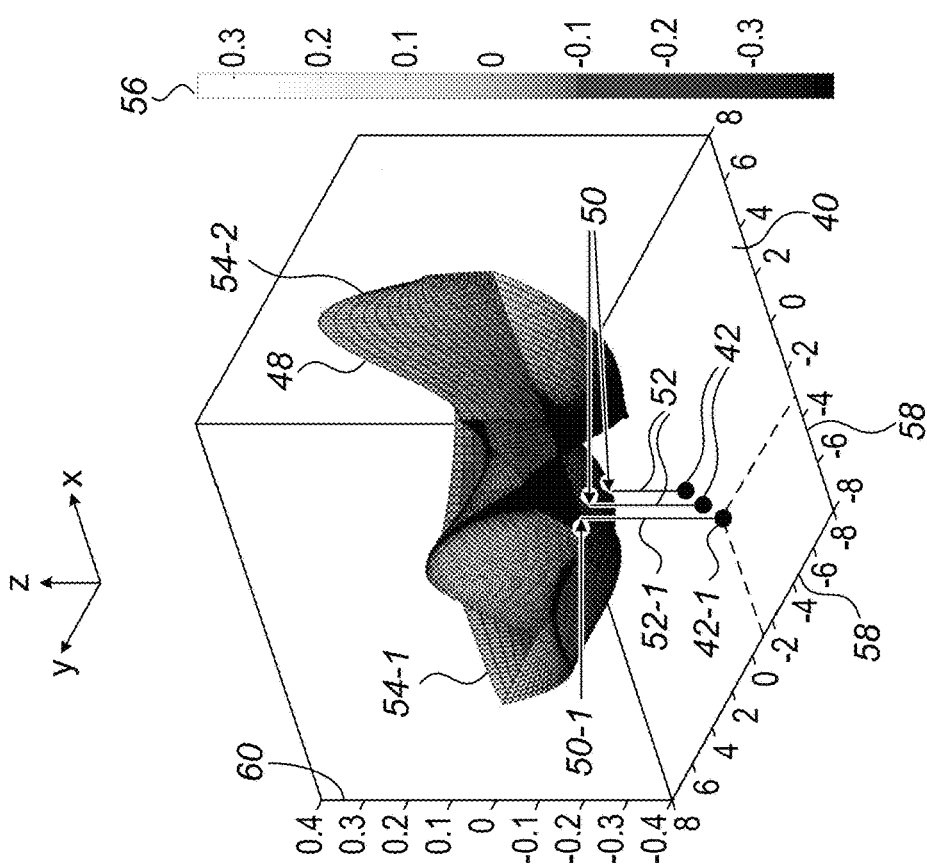

Reference is now made to FIG. 4A, which is a schematic view of a curved three-dimensional surface 48 describing electrical activity rendered by the system 10 of FIG. 1. FIG. 4A shows some of the positions 42 of the electrodes 32 (FIG. 2A) projected on the plane 40 which is on the x-y axes 58. For example, the position 42-1 of the electrode 32-1 (FIG. 2A) is shown on the plane 40. The sampled voltage of electrode 32-1 at time 1200 milliseconds is −0.1 millivolts, as illustrated in FIG. 3. A data point 50-1 of the three-dimensional surface 48 is derived from the position 42-1 and the associated sample voltage of −0.1 volts. A displacement 52-1 of the data point 50-1 from the plane 40 in a direction perpendicular to the plane 40 (e.g., along the z-axis 60) is computed based on the sampled voltage of the electrode 32-1 at time 1200 milliseconds. Similarly, respective data points 50 (only some shown for the sake of simplicity) are computed based on respective projected positions 42 and the computed respective displacements 52. The three-dimensional surface 48 is fitted to data points 50 using any suitable surface fitting method, which may include interpolation and optionally extrapolation based on the data points 50. FIG. 4A shows the x-y axes 58 and the z-axis 60 being labeled with suitable units of displacement, and voltage, respectively.

Regions 54 of the three-dimensional surface 48 have been colored with different colors according to the voltage values associated with the regions 54. For example, region 54-1 may be red, while region 54-2 may be yellow. FIG. 4A includes a legend 56 which provides a mapping between color and voltage values.

Figure 4D:
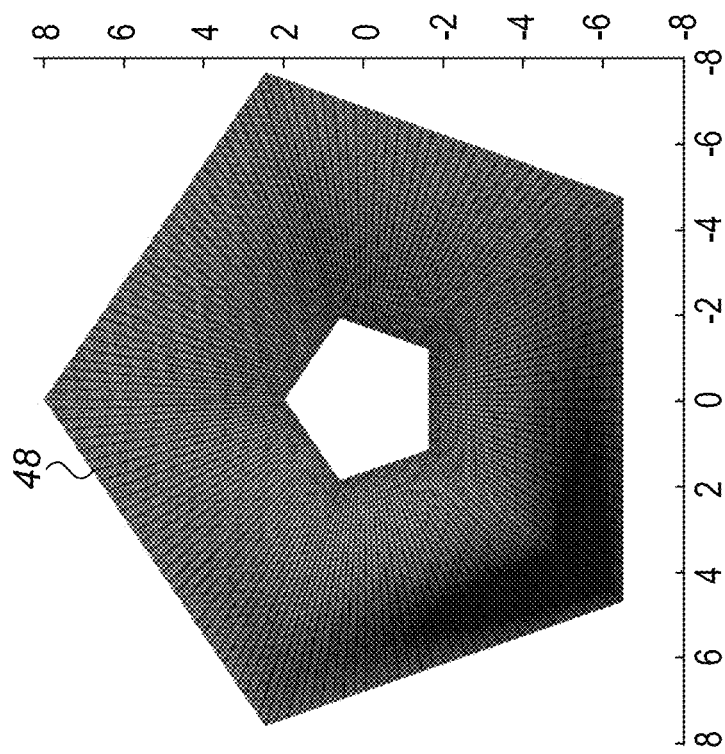
Figure 4C:
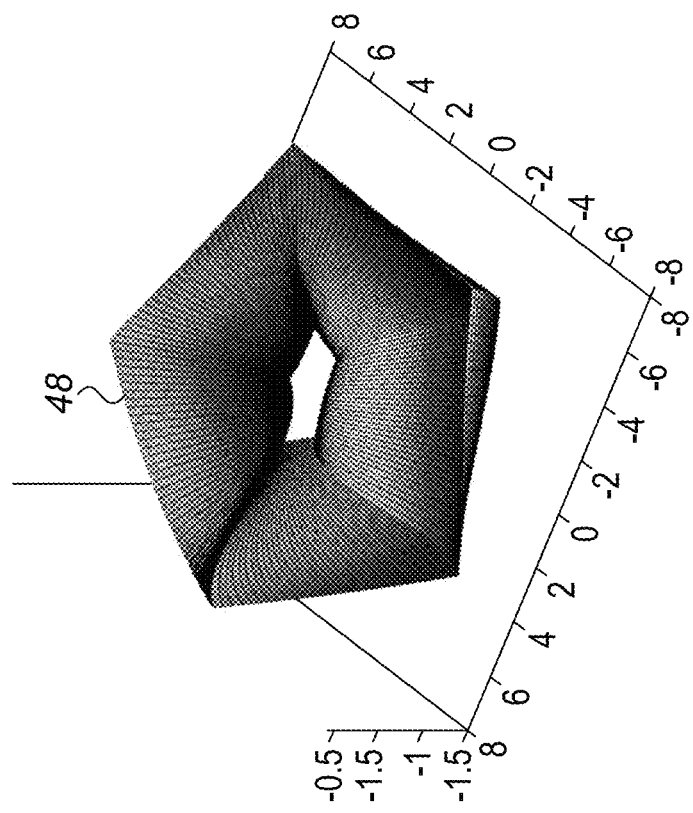
Figure 4F:
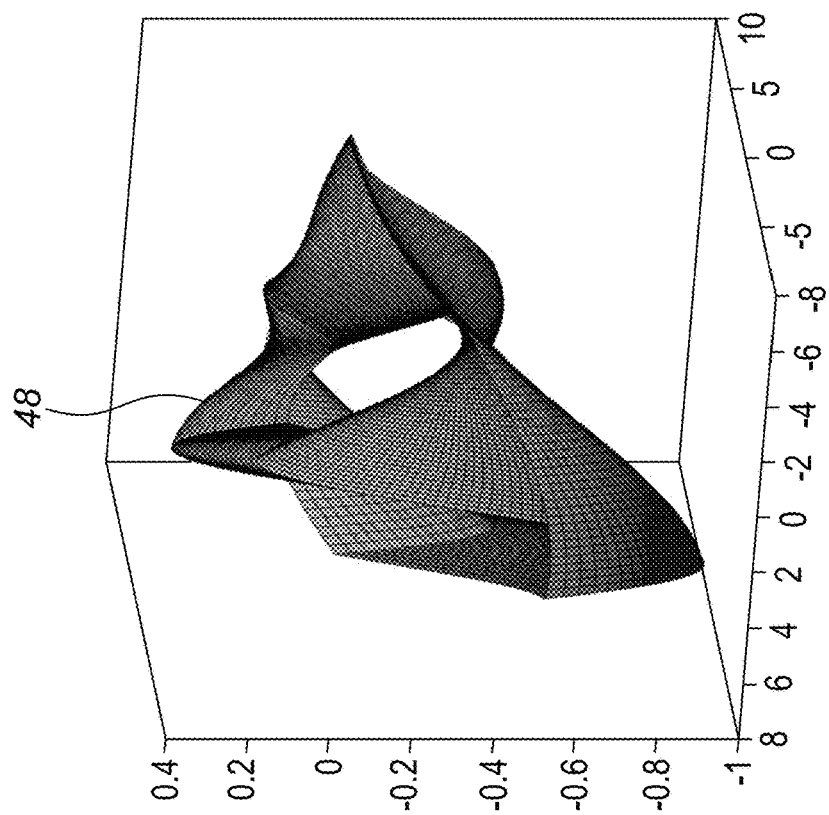
Figure 4E:
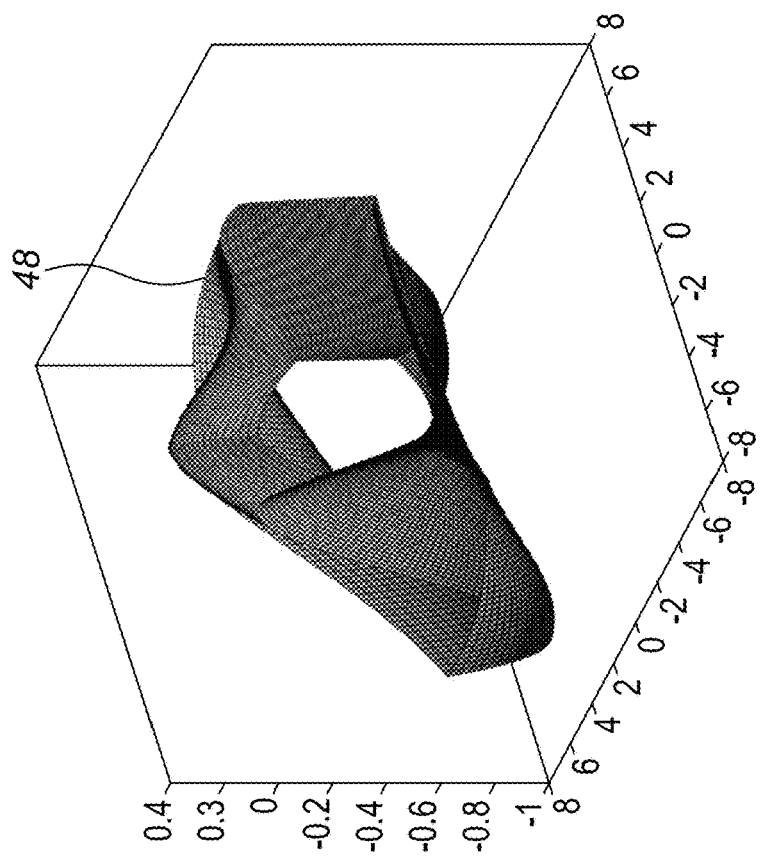

Reference is now made to FIGS. 4B-F, which are schematic views of curved three-dimensional surfaces 48 describing electrical activity rendered by the system 10 of FIG. 1. The three-dimensional surface 48 shown in FIG. 4B represents electrical activity over the electrodes 32 (FIG. 2A) at another sampling time, for example, at a sampling time of 1250 milliseconds. FIG. 4C shows more of the top of one of the three-dimensional surfaces 48. FIG. 4D shows one of the three-dimensional surfaces 48 directly from above so that the z-axis is not even visible. FIGS. 4E and 4F are further examples of three-dimensional surfaces 48.

Figure 5:
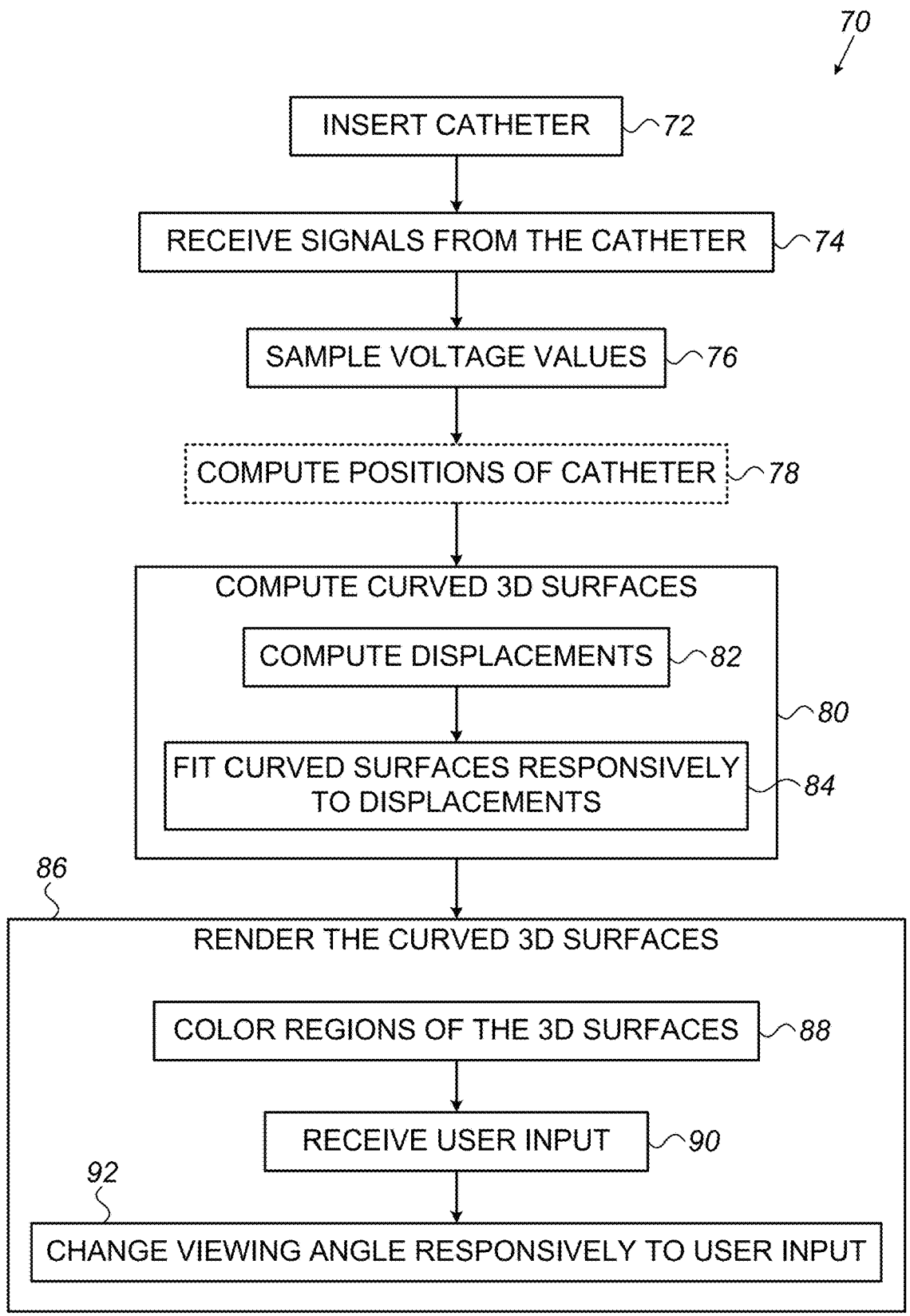
FIG. 5 is a flow-chart including steps in a method of operation of the system of FIG. 1.

Reference is now made to FIG. 5, which is a flow-chart 70 including steps in a method of operation of the system 10 of FIG. 1.

The catheter is inserted (block 72) into a chamber of the heart 12 (FIG. 1) of the living subject. Respective catheter electrodes 32 (FIG. 2A) contact tissue at respective locations within the chamber of the heart 12. Some of the catheter electrodes 32 may be in contact with the tissue while other electrodes 32 are not in contact with the tissue. In some cases, all the electrodes 32 may be in contact with the tissue.

The processing circuitry 22 (FIG. 1) is configured to receive (block 74) signals 46 (FIG. 3) from the catheter 14 (FIG. 1), and in response to the signals 46, sample (block 76) voltage values of the signals 46 at respective sampling times, compute respective curved three-dimensional surfaces 48 (FIGS. 4A-F), and render the three-dimensional surfaces 48 to the display 29. These steps are described in more detail below.

The signal 46 of each electrode 32 is typically sampled at each of the respective sampling times. In some embodiments, the processing circuitry is configured to sample the voltage values of the signals 46 at the respective sampling times at a rate exceeding ten times per second. In other embodiments, the sampling rate is less than, or equal to, ten times per second.

In some embodiments, the processing circuitry 22 is configured to compute (block 78) respective positions 42 (FIGS. 2A-B) of the respective catheter electrodes 32, for example, responsively to at least one signal received from a position transducer (not shown), which may be part of the catheter and/or part of an external apparatus such as body patches or an external position sensor. In other embodiments, the respective positions 42 of the respective catheter electrodes 32, used in the computations described below, are respective positions 42 derived from a static computer model of the catheter 14.

The respective positions 42 of the respective catheter electrodes 32 may be respective projected positions 42 projected onto the plane 40 (FIGS. 2A-B). In some embodiments, the respective positions 42 of the respective catheter electrodes 32 are respective projected positions 42 projected onto the plane 40, which is perpendicular to the axis 45 of the shaft 44 (FIGS. 2A-B).

The processing circuitry 22 is configured to compute (block 80) respective curved three-dimensional surfaces 48 (FIGS. 4A-F) describing electrical activity of the tissue over the catheter electrodes 32 at respective ones of the sampling times. It should be noted that any one of the three-dimensional surfaces 48 describes electrical activity for one of the sampling times and not multiple sampling times. The sampled voltages of different sampling times yield different three-dimensional surfaces 48. The three-dimensional surfaces 48 are computed responsively to: (a) respective positions 42 (e.g., represented by two-dimensional coordinates) of the respective catheter electrodes 32; and (b) the respective sampled voltage values indicative of electrical activity of the tissue that is sensed by the respective catheter electrodes 32 at the respective locations (on the tissue) at the respective sampling times.

In some embodiments, the processing circuitry 22 is configured to compute (block 82) respective displacements 52 (FIG. 4A), perpendicular to the plane 40 (FIG. 4A), from respective ones of the projected positions 42 of respective ones of the catheter electrodes 32 responsively to respective ones of the sampled voltage values at respective ones of the sampling times. The displacement 52 (in the z-axis 60 (FIG. 4A)) from the positions 42 (in the x-y axes 58 (FIG. 4A)) define the data points 50 (FIG. 4A) having x, y, z coordinates. The processing circuitry 22 is configured to fit (block 84) the respective curved three-dimensional surfaces 48 describing the electrical activity of the tissue over the catheter electrodes 32 at the respective ones of the sampling times, responsively to respective ones of the displacements 52, perpendicular to the plane 40, from respective ones of the projected positions 42. In other words, the processing circuitry 22 is configured to fit the respective curved three-dimensional surfaces 48 describing the electrical activity of the tissue over the catheter electrodes 32 at the respective ones of the sampling times, responsively to respective ones of the data points 50 (e.g., having x, y, z coordinates). For example, for one three-dimensional surface 48, the processing circuitry 22 is configured to compute respective displacements 52 (FIG. 4A), perpendicular to the plane 40 (FIG. 4A), from respective ones of the projected positions 42 of respective ones of the catheter electrodes 32 responsively to respective ones of the sampled voltage values at one sampling time yielding respective data points 50, and fit that curved three-dimensional surface 48 describing the electrical activity of the tissue over the catheter electrodes 32 at that sampling time, responsively to respective ones of the displacements 52 (i.e., the data points 50).

The processing circuitry 22 is configured to render (block 86) the respective three-dimensional surfaces 48 to the display 29 (FIG. 1) over time. In some embodiments, the processing circuitry 22 is configured to render the respective three-dimensional surfaces 48 to the display 29 over time with a new one of the three-dimensional surfaces 48 (e.g., corresponding to a next sampling time) being displayed at least every tenth of a second so that the rendered three-dimensional surfaces 48 provide an animation of an activation wave associated with the electrical activity of the tissue over the catheter electrodes 32. In some embodiments, the processing circuitry 22 is configured to render the respective three-dimensional surfaces 48 to the display 29 over time with a new one of the three-dimensional surfaces 48 being displayed at a rate less that every tenth of a second.

In some embodiments, the processing circuitry is configured to color (block 88) respective regions 54 (FIG. 4A) of the respective three-dimensional surfaces 48 responsively to respective ones of the sampled voltage values or respective ones of the displacements 52 (FIG. 4A).

The interface 39 (FIG. 1) is configured to receive (block 90) user input to change a viewing angle of ones of the three-dimensional surfaces 48. The processing circuitry 22 is configured to render (block 92) ones of the three-dimensional surfaces 48 with a different viewing angle responsively to the received user input.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical system, comprising:
a catheter configured to be inserted into a chamber of a heart of a living subject, and including catheter electrodes configured to contact tissue at respective locations within the chamber of the heart; and
processing circuitry configured to receive signals from the catheter, and in response to the signals:
sample voltage values of the received signals at a plurality of sampling times;
compute respective curved three-dimensional surfaces describing electrical activity of the tissue in contact with the catheter electrodes at each one of the plurality of sampling times, using only: (a) respective positions of the respective catheter electrodes represented by projected positions on a plane, the projected positions having two-dimensional x-y coordinates; and (b) the sampled voltage values of electrical activity of the tissue that is sensed by the associated catheter electrode at the respective locations at each of the plurality of sampling times, the sampled voltage values being represented by respective z-coordinates of the sampled voltage values, the z-coordinates being the displacement in a z-axis perpendicular from the x-y coordinates of the positions of the respective catheter electrodes responsively to respective ones of the sampled voltage values at respective ones of the sampling times, wherein each of the respective curved three-dimensional surfaces is fitted responsively to respective ones of the displacements; and render the respective three-dimensional surfaces to a display over time.

2. The system according to claim 1, wherein the processing circuitry is configured to color respective regions of the respective three-dimensional surfaces responsively to respective ones of the sampled voltage values.

3. The system according to claim 1, wherein the processing circuitry is configured to color respective regions of the respective three-dimensional surfaces responsively to respective ones of the displacements.

4. The system according to claim 1, wherein the processing circuitry is configured to:

sample the voltage values of the signals at the respective sampling times at a rate exceeding ten times per second; and render the respective three-dimensional surfaces to the display over time with a new one of the three-dimensional surfaces being displayed at least every tenth of a second so that the rendered three-dimensional surfaces provide an animation of an activation wave associated with the electrical activity of the tissue over the catheter electrodes.

5. The system according to claim 1, further comprising an interface configured to receive user input to change a viewing angle of one of the three-dimensional surfaces, wherein the processing circuitry is configured to render one of the three-dimensional surfaces with a different viewing angle responsively to the received user input.

6. The system according to claim 1, wherein:

the catheter comprises: a shaft having a distal end; and a distal end assembly on which the catheter electrodes are disposed; and the respective positions of the respective catheter electrodes are respective positions derived from a static computer model of the catheter.

7. The system according to claim 6, wherein the respective positions of the respective catheter electrodes are respective projected positions projected onto a plane perpendicular to an axis of the shaft.

8. The system according to claim 1, wherein:

the catheter comprises: a shaft having a distal end; and a distal end assembly on which the catheter electrodes are disposed; and the processing circuitry is configured to compute the respective positions of the respective catheter electrodes.

9. The system according to claim 8, wherein the respective positions of the respective catheter electrodes are respective projected positions projected onto a plane perpendicular to an axis of the shaft.

10. A medical method, comprising:

receiving signals from a catheter, which is configured to be inserted into a chamber of a heart of a living subject, and including catheter electrodes configured to contact tissue at respective locations within the chamber of the heart;

in response to the signals, sampling voltage values of the received signals at a plurality of sampling times;

computing respective curved three-dimensional surfaces describing electrical activity of the tissue in contact with the catheter electrodes at each one of the plurality of sampling times, using only: (a) respective positions of the respective catheter electrodes, the positions of the respective catheter electrodes being projected onto a plane defined by x-y coordinates, each catheter electrode position being projected in a direction parallel to a longitudinal axis of a shaft of the catheter and perpendicular to the plane, each catheter electrode position being represented by a pair of two-dimensional x-y coordinates in the plane; and (b) from each projected catheter electrode position, a computed displacement represented by a z-coordinate along a z-axis perpendicular to the x-y coordinate plane of the projected positions of the respective catheter electrodes responsively to respective ones of the sampled voltage values at respective ones of the sampling times, the computed displacements representing the sampled voltage values corresponding to the electrical activity of the tissue that is sensed by the associated catheter electrode at the respective locations at each of the plurality of sampling times, wherein each of the respective curved three-dimensional surfaces is fitted responsively to respective ones of the displacements; and rendering the respective three-dimensional surfaces to a display over time so that the rendered three-dimensional surfaces over time provide an animation of an activation wave associated with the electrical activity of the tissue in contact with the catheter electrodes.

11. The method according to claim 10, further comprising coloring respective regions of the respective three-dimensional surfaces responsively to respective ones of the sampled voltage values.

12. The method according to claim 10, further comprising coloring respective regions of the respective three-dimensional surfaces responsively to respective ones of the displacements.

13. The method according to claim 10, further comprising sampling the voltage values of the signals at the respective sampling times at a rate exceeding ten times per second, wherein the rendering includes rendering the respective three-dimensional surfaces to the display over time with a new one of the three-dimensional surfaces being displayed at least every tenth of a second so that the rendered three-dimensional surfaces provide an animation of an activation wave associated with the electrical activity of the tissue over the catheter electrodes.

14. The method according to claim 10, further comprising:

receiving user input to change a viewing angle of one of the three-dimensional surfaces; and rendering one of the three-dimensional surfaces with a different viewing angle responsively to the received user input.

15. The method according to claim 10, wherein:

the catheter comprises: a shaft having a distal end; and a distal end assembly on which the catheter electrodes are disposed; and the respective positions of the respective catheter electrodes are respective positions derived from a static computer model of the catheter.

16. The system according to claim 15, wherein the respective positions of the respective catheter electrodes are respective projected positions projected onto a plane perpendicular to an axis of the shaft.

17. The method according to claim 10, wherein the catheter comprises: a shaft having a distal end; and a distal end assembly on which the catheter electrodes are disposed, and the method further comprises computing the respective positions of the respective catheter electrodes.

18. The system according to claim 17, wherein the respective positions of the respective catheter electrodes are respective projected positions projected onto a plane perpendicular to an axis of the shaft.

19. A software product, comprising a non-transient computer-readable medium in which program instructions are stored, which instructions, when read by a central processing unit (CPU), cause the CPU to:

receive signals from a catheter, which is configured to be inserted into a chamber of a heart of a living subject, and including catheter electrodes configured to contact tissue at respective locations within the chamber of the heart;

in response to the signals, sample voltage values of the received signals at a plurality of sampling times;

compute respective curved three-dimensional surfaces describing electrical activity of the tissue in contact with the catheter electrodes at each one of the plurality of sampling times, using only: (a) respective positions of the respective catheter electrodes, the positions of the respective catheter electrodes being projected onto a plane defined by x-y coordinates, each catheter electrode position being projected in a direction parallel to a longitudinal axis of a shaft of the catheter and perpendicular to the plane, each catheter electrode position being represented by a pair of two-dimensional x-y coordinates in the plane; and (b) from each projected catheter electrode position, a computed displacement represented by a z-coordinate along a z-axis perpendicular to the x-y coordinate plane of the projected positions of the respective catheter electrodes responsively to respective ones of the sampled voltage values at respective ones of the sampling times, the computed displacements representing the sampled voltage values corresponding to the electrical activity of the tissue that is sensed by the associated catheter electrode at the respective locations at each of the plurality of sampling times, wherein each of the respective curved three-dimensional surfaces is fitted responsively to respective ones of the displacements; and render the respective three-dimensional surfaces to a display over time so that the rendered three-dimensional surfaces over time provide an animation wave associated with the electrical activity of the tissue in contact with the catheter electrodes.

* * * * *